United States Patent [19]
Purcell et al.

[11] Patent Number: 4,615,886
[45] Date of Patent: Oct. 7, 1986

[54] UTILIZING A HALOHYDROCARBON CONTAINING DISSOLVED WATER TO INACTIVATE A LIPID VIRUS

[75] Inventors: Robert H. Purcell, Boyds, Md.; Stephen M. Feinstone, Washington, D.C.

[73] Assignee: The United States of America as represented by the Secretary of the Department of Health & Human Services, Washington, D.C.

[21] Appl. No.: 611,752

[22] Filed: May 18, 1984

Related U.S. Application Data

[63] Continuation-in-part of Ser. No. 528,258, Aug. 31, 1983, Pat. No. 4,581,231, which is a continuation-in-part of Ser. No. 386,991, Jun. 10, 1982, Pat. No. 4,511,556.

[51] Int. Cl.[4] .......... A61K 35/14
[52] U.S. Cl. .......... 424/101; 514/2
[58] Field of Search .......... 424/89, 101; 435/238; 514/2; 260/112 B

[56] References Cited

U.S. PATENT DOCUMENTS

| | | | |
|---|---|---|---|
| 3,847,737 | 11/1974 | Kanarek . | |
| 4,031,204 | 6/1977 | Davis | 424/90 |
| 4,113,712 | 9/1978 | Funakoshi | 260/112 R |
| 4,139,630 | 2/1979 | Asculai et al. | 514/461 |
| 4,302,444 | 11/1981 | Baxendale | 424/89 |
| 4,314,997 | 2/1982 | Shanbrom | 424/101 |
| 4,315,919 | 2/1982 | Shanbrom | 514/1 |
| 4,405,603 | 9/1983 | Schwinn et al. | 424/101 |
| 4,424,206 | 1/1984 | Ohmura et al. | 424/101 |
| 4,446,134 | 5/1984 | Naito et al. | 424/101 |
| 4,456,590 | 6/1984 | Rubinstein | 424/101 |
| 4,481,189 | 11/1984 | Prince | 424/101 |
| 4,511,556 | 4/1985 | Purcell et al. | 424/89 X |

OTHER PUBLICATIONS

Purcell, Viral Hepatitis, 1981, International Symposium, Szmuness et al (eds) Franklin Inst. Press, Phil., pp. 3–12.

Philipson, Methods in Virology, Maramorosch et al (eds), vol. II, 1967, pp. 235–244.

Feinstone et al, Infection and Immunity, vol. 41, Aug. 1983, pp. 816–821.
Maramorosch et al., *Methods in Virology,* vol. II, Ch. 7, Academic Press, N.Y., 1967.
Purcell, "The Hepatitis Viruses: An Overview and Historical Perspective", *Viral Hepatitis,* Franklin Institute Press, Phila., 1981.

*Primary Examiner*—Robert J. Warden
*Assistant Examiner*—Shawn P. Foley
*Attorney, Agent, or Firm*—John S. Roberts, Jr.

[57] ABSTRACT

A method of inactivating a lipid virus contained in a dry protein carrier by contacting said virus-containing protein carrier for an abbreviated period of time at from 4°–40° C. with a composition including a halohydrocarbon treating agent and water dissolved in said treating agent. Preferred lipid viruses are Hepatitis B virus (HBV) and non-A, non-B Hepatitis (NANBH) virus.

11 Claims, No Drawings

UTILIZING A HALOHYDROCARBON CONTAINING DISSOLVED WATER TO INACTIVATE A LIPID VIRUS

This application is a continuation in part of pending patent application Ser. No. 528,258 filed Aug. 31, 1983, now U.S. Pat. No. 4,581,231, which is a continuation-in-part of patent application Ser. No. 386,991 filed June 10, 1982, now U.S. Pat. No. 4,511,556.

This invention relates to a method of inactivating a lipid virus contained in a dry protein carrier by contacting said virus-containing protein carrier for an extended period of time and ambient temperature with a halohydrocarbon solvent or treating agent, preferably chloroform, which contains dissolved water in an amount between 75% and 100% of that amount required to saturate the solvent at the ambient temperature. Preferred viruses are Hepatitis B virus (HBV) and non-A, non-B Hepatitis (NANBH) virus.

GENERAL BACKGROUND

A selected lipid type virus, viral hepatitis, has been recognized as an important and serious sequela of parenteral exposure to blood and blood components since the early 1940s. It was originally believed that all such blood-associated hepatitis was caused by the serum hepatitis virus (now called the Hepatitis B virus, or HBV). Subsequently, the development of sensitive assays for infection with this virus revealed that only approximately one-third of transfusion-associated hepatitis was caused by the HBV. It was thought that the remaining hepatitis was caused by the Hepatitis A virus (HAV). However, the development of sensitive assays for HAV led to the recognition of a new hepatitis virus, the non-A, non-B hepatitis virus (NANB) in 1975. The successful application of sensitive screening tests for HBV to blood donors has resulted in a decrease (but not disappearance) of HBV in transfusion-associated hepatitis; at present approximately 90% of such hepatitis is caused by non-A, non-B agents.

Similarly, hepatitis following administration of plasma protein derivatives such as antihemophilic factor was thought to be caused solely by HBV. However, in the late 1970s, the association of NANB agents with administration of antihemophilic factor to hemophiliacs was reported and confirmed. As with transfusion-associated hepatitis, the application of serologic screening methods to plasma donors has resulted in a relative decrease in the importance of HBV in such blood product-associated hepatitis.

Non-A, non-B hepatitis is the major cause of transfusion associated hepatitis in the United States Presently, less than 10% of post-transfusion cases are caused by the hepatitis B virus. Of the remainder, cytomegalovirus may account for a small proportion but the vast majority are caused by an as yet unidentified agent. There is a large amount of evidence supporting a transmissible agent as the cause of NANBH. This includes transmission studies done in both humans and non-human primates. Chimpanzees and marmoset monkeys have both been shown to be susceptible to infection by at least some NANBH agents. Though very costly and cumbersome to work with, these animals can be used to aid in the characterization of the infectious agent of NANBH.

Unfortunately, serologic tests for the detection of NANB agents are not available for detection of potentially infectious donors because the agents have not been adequately identified and characterized despite extensive efforts to do so. Therefore, blood and plasma protein derivative products remain potential sources for transmission of hepatitis agents to recipients. The resultant hepatitis can be quite serious, even life-threatening, and can result in not only acute hepatitis but also chronic hepatitis in a significant proportion of cases.

For these reasons, attempts to inactivate hepatitis agents in blood and plasma products have been pursued with vigor. Such approaches have included the use of heat, the addition of anti-HBV antibody, the use of solid immunoadsorbents or other chemical-specific adsorbents, exposure to ultraviolet radiation, the addition of certain inactivating substances, such as beta-propriolactone, surface-active substances, etc. None of the approaches has been entirely successful and some have introduced an added potential risk (e.g., beta-propriolactone is carcinogenic). Failure of these approaches stems from relative resistance of the agents to physical or chemical inactivation, particularly when in the presence of high protein concentrations as occurs with blood products and from limited knowledge about the nature of the hepatitis agents, especially the NANB agents.

As part of a systematic characterization of NANB agents by standardized virologic methods, the present inventors first established that HBV and at least one NANB agent contain lipids essential for the integrity and viability of the viruses. This was established by exposing the viruses to a potent lipid solvent (chloroform) and demonstrating that such chloroform-extracted viruses were rendered non-infectious in a suitable susceptible host, the chimpanzee (*Pan troglodytes*).

It was later found that when viruses were contained in a dried protein carrier such as a commercial factor VIII concentrate preparation, the viruses were much more difficult to inactivate with the lipid solvent than when the protein carrier was reconstituted to a liquid with water and then treated with the lipid solvent. It was also found that the biologic activity of the protein carrier was difficult to maintain when it was treated as a liquid with the lipid solvent. Thus, this invention expands the parent invention by modifying the process in such a way that a lipid virus contained a dry protein carrier, in particular a plasma derivative, can be readily and consistently inactivated by a lipid solvent while the biologic activity of the plasma product is maintained at a high level.

The present invention relates to a method of inactivating lipid viruses that frequently contaminate a plasma protein product. Said viruses are most frequently hepatitis B virus and non-A, non-B hepatitis virus but are also defined to include members of the herpesvirus group (cytomegalovirus, Epstein-Barr virus, herpes zoster virus, herpesvirus type 1 and type 2), the delta agent (a type of non-A, non-B hepatitis virus), togaviruses (including rubella virus), bunyaviruses, retroviruses (including the human T-cell leukemia viruses), orthomyxoviruses (including influenza), paramyxoviruses (measles, mumps), rhabdoviruses (rabies, Marburg agent), arenaviruses (Lassa fever, other hemorrhagic fevers), coronaviruses, hepadnaviruses, and poxvirus group (smallpox, vaccinia virus). Other viruses, known or suspected, such as the putative agent of acquired imune deficiency syndrome (AIDS) are included as viruses possibly containing essential lipids.

(Evidence that the agent of AIDS is a retrovirus has recently been published.)

The plasma protein product is defined as a protein derived from blood or blood plasma that is intended for human medical uses most often to correct a deficiency of that particular blood protein, or as an aid to treating some disease that might benefit from an increased concentration of the particular blood protein. Over 100 such plasma proteins have been identified and perhaps many more will eventually be found (cf. Putnam, *Plasma Proteins,* pp. 36–41 and Table 1). Examples of such blood products are antihemophilic factor (factor VIII), factor IX, fibrinogen, fibronectin, albumin, complement components, plasminogen, transferrin, and haptoglobin, and many other plasma proteins that have indicated medical uses but that may not at this time be marketed. In general, lipoproteins would not survive the process of this invention in their native state. In addition, certain blood proteins that are not intended for therapeutic use but may be used, for example, in diagnostic tests, may also be treated to reduce their hazard to the person handling them. Such plasma protein products are often dried by lyophilization during the manufacture process in order to preserve their biologic potency, increase shelf life and for ease of handling and shipping. The residual moisture content of such dried products ranges between about 0.5 and 1.5%.

In the present invention the contaminating lipid containing viruses are inactivated by treating (extracting or contacting) the dry plasma product with a lipid solvent in which water has been dissolved such that the lipid solvent contains between about 75% to 100% of the amount of water required to reach its dissolved water saturation point. The preferred lipid solvent is chloroform ($CHCl_3$) or $CHCl_3$ and a lower alcohol (e.g., methanol or ethanol), or the fluorocarbons (trichlorotrifluoroethane) which include the most common agents such as $CCl_3F$, $CH_2F_2$, $CCl_2F_2$, $CCl_2FCClF_2$ and others sold under the trademark registration Freon ® or Genetron ®. Throughout the present invention the biologic activity of the plasma protein is retained but the infectivity of the virus is removed.

The period of time for the treatment is about 10 minutes to about 10 hours and at least about 10 minutes. The temperature of the treatment is from about 4° C. to 40° C.

The quantity of lipid solvent used to treat dried plasma product is from about equal to the weight of the dry blood product to about 1,000 times the weight of the dry blood product.

The lipid solvent or the treating agent may be removed from the plasma product by evaportion with a stream of pure, dry nitrogen gas ($N_2$), by vacuum evaporation or by a combination of these or other physical methods which returns the plasma product to the dry state and free of the lipid solvent.

Commercial chloroform contains 0.5% (v/v) ethanol as a stabilizer. The quantity of dissolved water required to saturate pure chloroform varies between 0.019% (wt/v) at 3° C. to 0.065% at 22° C. to 0.118% at 43° C. (Stephen and Stephen (eds.), *Solubilities of Inorganic and Organic Compounds,* Vol. 1, MacMillan Co., New York, 1963, p. 370). Therefore, the absolute quantity of water in the chloroform can be increased by increasing the temperature. In addition, the quantity of dissolved water can be increased by increasing the ethanol concentration.

It has been found that dry (water-free) chloroform is inconsistently effective in inactivating vaccinia virus. It is believed that increases in the dissolved water content of the treating agent tend to increase the effectiveness of the inactivation treatment, with superior results achieved as the water dissolved in the treating agent approaches 100% saturation of the treating agent at the temperature of treatment. It is believed that inactivation treatments should be conducted at saturation levels of from about 75 to about 100%. A two-phase system including water and treating agent, while relatively effective in inactivating virus, may destroy activity of blood products, such as Factor VIII.

MATERIAL INFORMATION DISCLOSURE

A review of the prior art of patents is as follows:

U.S. Pat. No. 4,113,712 Funakoshi—Utilization of a surfactant such as the Tritons or Tweens for hepatitis B surface antigen particles.

U.S. Pat. No. 4,139,630 Asculai et al—Utilization of non-ionic surfactants as inactivating agents for herpes simplex virus.

U.S. Pat. No. 4,314,997 Shanbrom—A non-denaturing amphiphile used to inactivate hepatitis viruses B and non-A, non-B in amount of 0.25–10% by weight and citing non-anionic, anionic, and cationic surfactants.

U.S. Pat. No. 3,847,737 Kanarek—A method of inactivating myxoviruses by utilizing a treating composition consisting of Tween 20, 40, 60 or 80, e.g., a polyoxyethylene ester of partial oleic acid together with an organic solvent consisting of a chlorinated lower hydrocarbon having 2–5 carbon atoms.

U.S. Pat. No. 4,315,919 Shanbrom—Similar disclosure to 4,314,997 above.

U.S. Pat. No. 4,031,204 Davis—This patent notes at column 4 that a 50% chloroform concentration will inactivate totally the feline viral rhinotracheitis ($FVR_m$) virus.

U.S. Pat. No. 4,302,444 Baxendale—This patent indicates that for a vaccine for protecting against egg drop disease, the inactivation can be carried out with formaldehyde, with organic solvents, particularly halogenated hydrocarbons in the presence of a surface active agent, such as a polyoxy ethylene sorbitan mono-oleate or with beta-propriolactone.

Non-patent literature is as follows:

Purcell, "The Hepatitis Viruses: An Overview and Historical Perspective," Viral Hepatitis, 1981, International Symposium, Szmuness, Alter and Maynard (eds.), Franklin Institute Press, Philadelphia, pp. 3–12.

Philipson, "Water-Organic Solvent Phase Systems," Methods in Virology, Maramorosch et al (eds.), Vol. II, 1967, pp. 235–244.

Feinstone et al, "Inactivation of Hepatitis B Virus and Non-A, Non-B Hepatitis by Chloroform," *Infection and Immunity,* Vol. 41, August 1983, pp. 816–821.

EXAMPLE 1

Vaccinia virus, a member of the pox virus group was used as an example of lipid-containing viruses. The pox viruses are known to be the most difficult group of lipid-containing viruses to inactivate by lipid solvents.

A sealed ampoule of lyophilized vaccinia virus, Elstree Strain ATCC #VR-862, was obtained from the American Type Culture Collection. The dry contents of the single ampoule were removed, divided into four approximately equal parts and placed into pre-weighed vials. The vials were then re-weighed to determine the weight of the dry powder containing the vaccinia virus. The vials were numbered 1, 2, 3 and 4 and they were then treated as follows:

Vial #1—1 ml of chloroform from a freshly opened bottle (J. T. Baker Chemical #9180-1).

Vial #2—1 ml of chloroform (from an identical bottle) that had been saturated with water by shaking it for four hours with water; then allowing the phases to separate upon standing overnight.

Vial #3—0.34 ml $H_2O$ (0.236 ml $H_2O$/mg of vaccinia powder) was added to dissolve the vaccinia powder; then 0.66 ml fresh chloroform was added.

Vial #4—0.446 ml $H_2O$ (0.236 ml/mg vaccinia powder) was added to dissolve the vaccinia powder.

All vials were then placed on a rotary shaker and were shaken vigorously for four hours at room temperature (approximately 20° C.).

The chloroform in vials #1 and #2 was evaporated off by a stream of purified, dry $N_2$ gas. The aqueous (upper) phase was pipetted off the chloroform in vial #3. Vial #4 was not further treated. All vials were stored at $-70°$ C. until infectivity testing was performed.

The amount of infectious vaccinia virus remaining after the various treatments was assayed by tissue culture infectivity using BSC-1 cells. Quadruplicate wells of 24-well tissue culture plates containing monolayers of BSC-1 cells were inoculated with serial 10-fold dilutions of the vaccinia virus suspensions after they were treated. The BSC-1 cells were examined microscopically for the typical cytopathic effect produced by vaccinia virus.

Factor VIII concentrate (Koate, Cutter Laboratories) was treated in a way similar to the vaccinia virus in order to test for retention of Factor VIII activity following extraction by chloroform. Factor VIII activity was determined by a commercial laboratory using standard techniques.

Results
The results are summarized in the following table.

| Sample No. | Treatment | Vaccinia Titer ($TCID_{50}$) | Factor VIII Retention* (% of control) |
|---|---|---|---|
| 1 | Dry chloroform | $10^5$ | 75.6 |
| 2 | $H_2O$ Sat $CHCl_3$ | $10^{0.5}$ | 75.6 |
| 3 | $H_2O$ + $CHCl_3$ (2 phase) | $10^{1.25}$ | 15.0 |
| 4 | $H_2O$ only (control) | $10^{5.25}$ | 100.0 |

*Compared to non-chloroform treated control (sample #4)

Interpretation

The dry chloroform was not effective in inactivating the dry vaccinia virus. The two-phase system and the water saturated $CHCl_3$ were effective inactivators of vaccinia. However, the two-phase (aqueous and $CHCl_3$) system also destroyed approximately 85% of the Factor VIII activity. Treatment of dry Factor VIII with either the dry $CHCl_3$ or the water saturated $CHCl_3$ resulted in a retention of 75% of the Factor VIII activity.

Thus, it was shown that vaccinia virus in the lyophilized state could be readily inactivated by chloroform if the chloroform was first saturated with water. The pox virus group, of which vaccinia virus is a member, is known to be the group of viruses containing essential lipids that is the most difficult to inactivate by lipid solvents such as chloroform. Therefore, it can be reasoned that other viruses that contain essential lipids will also be readily inactivated in the dry state by the process of extracting them with chloroform that has been saturated in dissolved water.

EXAMPLE 2

The purpose of this experiment was to determine the degree of $H_2O$ saturation of the chloroform required to effectively kill viruses contained in a dry powder. Vaccinia virus and Factor VIII concentrate were treated in various ways similar to the methodology of Example 1. The treatments were as follows:

(1) $CHCl_3$ 100% saturated by water
(2) $CHCl_3$ 75% saturated by water
(3) $CHCl_3$ 50% saturated by water
(4) $CHCl_3$ 25% saturated by water
(5) $CHCl_3$ fresh, dry from a newly opened bottle of the same lot # as in 1-4
(6) Fresh dry $CHCl_3$+water in a two-phase system
(7) Water only The $CHCl_3$ that contained water at less than the saturation level was prepared by mixing appropriate volumes of 100% water-saturated $CHCl_3$ with dry $CHCl_3$ from a freshly opened bottle. In this way the desired saturation percent was easily achieved. Vials containing the dry vaccinia powder or the Factor VIII concentrate powder and the appropriate treating agent were shaken vigorously on a rotary shaker at room temperature (approximately 20° C.) for 4 hours. The $CHCl_3$ was evaporated off by a stream of nitrogen gas or the aqueous phase was separated from the $CHCl_3$ by centrifuging at 1000 RPM for 10 minutes and the aqueous phase (top layer) was carefully pipetted off. The redried powders were reconstituted with a measured amount of water so that 0.2 ml of water was added per mg of vaccinia powder and 0.05 ml of water was added per mg of Factor VIII powder. The samples were then stored frozen at $-70°$ C. until testing.

Vaccinia and Factor VIII were tested as described in Example 1.

| Results | | |
|---|---|---|
| Treatment | Vaccinia Titer ($TCID_{50}$) | Factor VIII Level (% of Control) |
| 100% $H_2O$ saturated $CHCl_3$ | $10^{2.25}$ | 105% |
| 75% $H_2O$ saturated $CHCl_3$ | $10^{4.75}$ | 100 |
| 50% $H_2O$ saturated $CHCl_3$ | $10^{4.25}$ | 100 |
| 25% $H_2O$ saturated $CHCl_3$ | $10^{4.75}$ | 110 |
| Dry fresh $CHCl_3$ | $10^4$ | 110 |
| $H_2O$ + $CHCl_3$ (2 phase) | 0 | 14 |
| $H_2O$ only | $10^{4.5}$ | 100 |

Interpretation

Essentially 100% of the vaccinia virus was killed in the two-phase system but 80% of the Factor VIII was destroyed. With 100% $H_2O$ saturated $CHCl_3$ greater than 99% of the vaccinia was killed and there was complete retention of all Factor VIII activity compared to the control. However, when the content of the dissolved water was reduced to 75% or less of the saturation level, there was essentially no virus killing although the Factor VIII activity was maintained. It must be concluded that greater than 75% of the water saturation level of $CHCl_3$ must be achieved in order to effectively kill the virus in the dry state.

EXAMPLE 3

The purpose of this experiment was to test if increasing the H₂O content of the chloroform treating agent would improve virus killing. This was accomplished by saturating the chloroform with water at a higher temperature (37°) which increases the amount of water that can be dissolved in the chloroform before saturation is achieved. The treatment was also performed at 37°.

The second method used to increase the water content was to increase the ethanol content of the chloroform. Commercial chloroform contains about 0.5% (v/v) ethanol as a preservative. The water content of the chloroform can be increased by increasing the ethanol content of the chloroform. In this experiment the ethanol content was increased from 0.5% to 2% and 5% and then the chloroform/ethanol was saturated with water. The treatment protocol was similar to those in Examples 1 and 2 in which weighed, lyophylized vaccinia powder and weighed, lyophylized Factor VIII concentrate were treated with the various chloroform preparations or water only as a control. Treatment was for 4 hours at the temperature stated in the protocol. Chloroform was removed by evaporation with a stream of pure, dry nitrogen gas or in the case of water/chloroform two-phase systems by centrifuging at 1000 RPM for 10 minutes and then pipetting off the aqueous phase. Dried powder was reconstituted with H₂O at 0.2 ml/mg of powdered vaccinia and 0.05 ml/mg powdered Factor VIII.

| | Protocol | | Post Treatment | |
|---|---|---|---|---|
| Vial # | Treatment | Temp. | Vaccinia Titer $TCID_{50}$ | Factor VIII Levels % of Control |
| 1 | Dry CHCl₃ | 20° C. | $10^5$ | 75 |
| 2 | Water saturated CHCl₃ | 20° C. | 0 | 94 |
| 3 | Dry CHCl₃ | 37° C. | $10^{4.75}$ | 119 |
| 4 | H₂O saturated CHCl₃ | 37° C. | 0 | 75 |
| 5 | Dry CHCl₃ - 2% ethanol | 20° | $10^5$ | 100 |
| 6 | H₂O saturated CHCl₃ - 2% ethanol | 20° | 0 | 100 |
| 7 | Dry CHCl₃ - 5% ethanol | 20° | $10^{4.75}$ | 119 |
| 8 | H₂O saturated CHCl₃ 5% ethanol | 20° | 0 | 96 |
| 9 | CHCl₃ + H₂O 2-phase | 20° | 0 | 0.3 |
| 10 | CHCl₃ + H₂O 2-phase | 37° | 0 | 0.3 |
| 11 | H₂O only (control) | 20° | $10^{5.5}$ | 100 |
| 12 | H₂O only | 37° | $10^{5.5}$ | 15 |

Interpretation

Chloroform saturated with water killed all of the $10^{5.5}$ infectious vaccinia viruses in the lyophylized dry powder. Chloroform without dissolved water at or near the saturation point killed less than 10% of the infectious vaccinia virus and was therefore poorly effective in killing the vaccinia virus. Increasing the temperature or ethanol content of the chloroform had little effect on virus killing if the chloroform or the chloroform alcohol were not also saturated with water. While water and chloroform together in a two-phase system was effective in virus killing, it also destroyed most of the Factor VIII activity. Factor VIII activity was maintained when the chloroform treatment was performed in a one-phase system whether or not the chloroform or chloroform/ethanol was saturated with water.

It is concluded from Examples 1, 2, and 3 that lipid containing viruses contained in a dry protein powder can be killed by the lipid solvent, chloroform if the chloroform is saturated with water. The water saturation point of chloroform can be increased by increasing the temperature or by adding ethanol. However, virus killing is effective as long as the dissolved water content approaches the saturation point at the temperature or ethanol level used. It is further concluded that a blood product such as Factor VIII that is commonly prepared as a dry powder can be treated as a dry powder with water saturated chloroform without a significant loss of activity.

We claim:

1. A method of inactivating viruses that contain essential lipids in a dried plasma protein product comprising contacting said protein product for at least about 10 minutes at a treatment temperature of about 4° C.-40° C. with a treating composition consisting essentially of (a) a treating agent selected from one member of the group consisting of halogenated hydrocarbons and ethers and (b) water dissolved in said treating agent wherein said water is about 75-100% of the amount of water required to saturate the treating agent at the treatment temperature; and removing the treating agent from the protein product.

2. The method of claim 1 wherein said protein product is contacted with said treating agent from about 10 minutes to about 10 hours.

3. The method of claim 1 wherein the said viruses are selected from at least one member of the group consisting of Hepatitis B virus (HBV) and non-A, non-B hepatitis virus (NANBH).

4. The method of claim 1 wherein the said viruses are selected from at least one member of the lipid-containing groups consisting of herpesviruses, the delta agent, togaviruses, bunyaviruses, retroviruses, ortho-myxoviruses, paramyxoviruses, rhabdoviruses, poxviruses, hepadnaviruses, arenaviruses, and coronaviruses.

5. The method of claim 1 wherein the treating agent is chloroform.

6. The method of claim 1 wherein the treating agent is removed from the protein product by evaporation.

7. The method of claim 1 wherein the water content of the treating agent is adjusted by controlling the temperature of treatment.

8. A method of inactivating viruses that contain essential lipids in a dried plasma protein product comprising contacting said protein product for at least about 10 minutes at a treatment temperature of about 4° C.-40° C. with a treating composition consisting essentially of a solution of chloroform and an alcohol formed by dissolving alcohol in the chloroform and then dissolving water in the chloroform-alcohol solution; and removing the treating agent from the protein product.

9. The method of claim 8 wherein the treating composition is chloroform containing ethanol and the dissolved water content of the solution is adjusted to the amount necessary for 100% saturation of the chloroformethanol solution at the treatment temperature.

10. A process for inactivating a lipid virus in a dried blood- or plasma-derived protein product comprising contacting said protein product for at least about 10 minutes at a temperature of about 4° C. to about 40° C. with a solution of chloroform 100% saturated with water; and removing the chloroform from the protein product.

11. A method of claim 10 wherein the biologic activity of the blood- or plasma-derived protein product is retained by the treatment although lipid viruses contained in said product are inactivated.

* * * * *